US00PP35176P2

(12) United States Plant Patent
Olesen

(10) Patent No.: US PP35,176 P2
(45) Date of Patent: May 23, 2023

(54) ROSE PLANT NAMED 'POULREN034'

(50) Latin Name: *Rosa hybrida*
Varietal Denomination: Poulren034

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 17/803,612

(22) Filed: Sep. 13, 2022

(51) Int. Cl.
*A01H 5/02* (2018.01)
*A01H 6/74* (2018.01)

(52) U.S. Cl.
USPC ..... Plt./103

(58) Field of Classification Search
USPC ..... Plt./101, 102, 103
See application file for complete search history.

(56) References Cited

PUBLICATIONS

Poulsen Roser. 2020. Baroniet Rosendal. https://www.poulsenroser.dk/en/Roses/ShowProduct/67452. 1 page (Year: 2020).*

* cited by examiner

*Primary Examiner* — Karen M Redden

(57) ABSTRACT

A new garden rose plant of the Hybrid Tea class which has abundant, white flowers and attractive foliage. This new and distinct variety has shown to be uniform and stable in the resulting generations from asexual propagation.

2 Drawing Sheets

Botanical designation: *Rosa hybrida.*

Variety denomination: 'Poulren034'.

This application claims priority to Plant Breeder's Rights Application Number 2021/2359, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulren034', originated as a single seedling from the stated cross.

The new variety may be distinguished from its male pollen parent and female seed parent primarily by the following characteristics. The male pollen parent plant has salmon colour flowers while the new variety has white flowers. The female seed parent plant has yellow flowers while the new variety has white flowers.

The objective of the hybridization of this rose variety was to create a new and distinct variety with unique qualities, such as:

1. Uniform and abundant white flowers;
2. Vigorous, but compact growth when propagated on its own roots;
3. Perfumed flowers; and
4. Exceptional disease resistance.

This combination of qualities is not present in previously available commercial cultivars of this type, known to the inventor, and distinguish 'Poulren034' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulren034' was selected in the spring of 2014 by the inventor as a single plant from the progeny of the aforementioned hybridization.

Asexual reproduction of 'Poulren034' by rooted cuttings was first done by Mogens N. Olesen in the nursery in Fredensborg, Denmark in July, 2014. This initial and other subsequent asexual propagations conducted in controlled environments have demonstrated that the characteristics of 'Poulren034' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren034'.

Specifically illustrated in FIG. 1 of the drawings are an open flower viewed from above, petals detached revealing reproductive flower parts, sepals detached, flower bud, and pedicel.

DETAILED DESCRIPTION OF THE VARIETY

Figure 1:
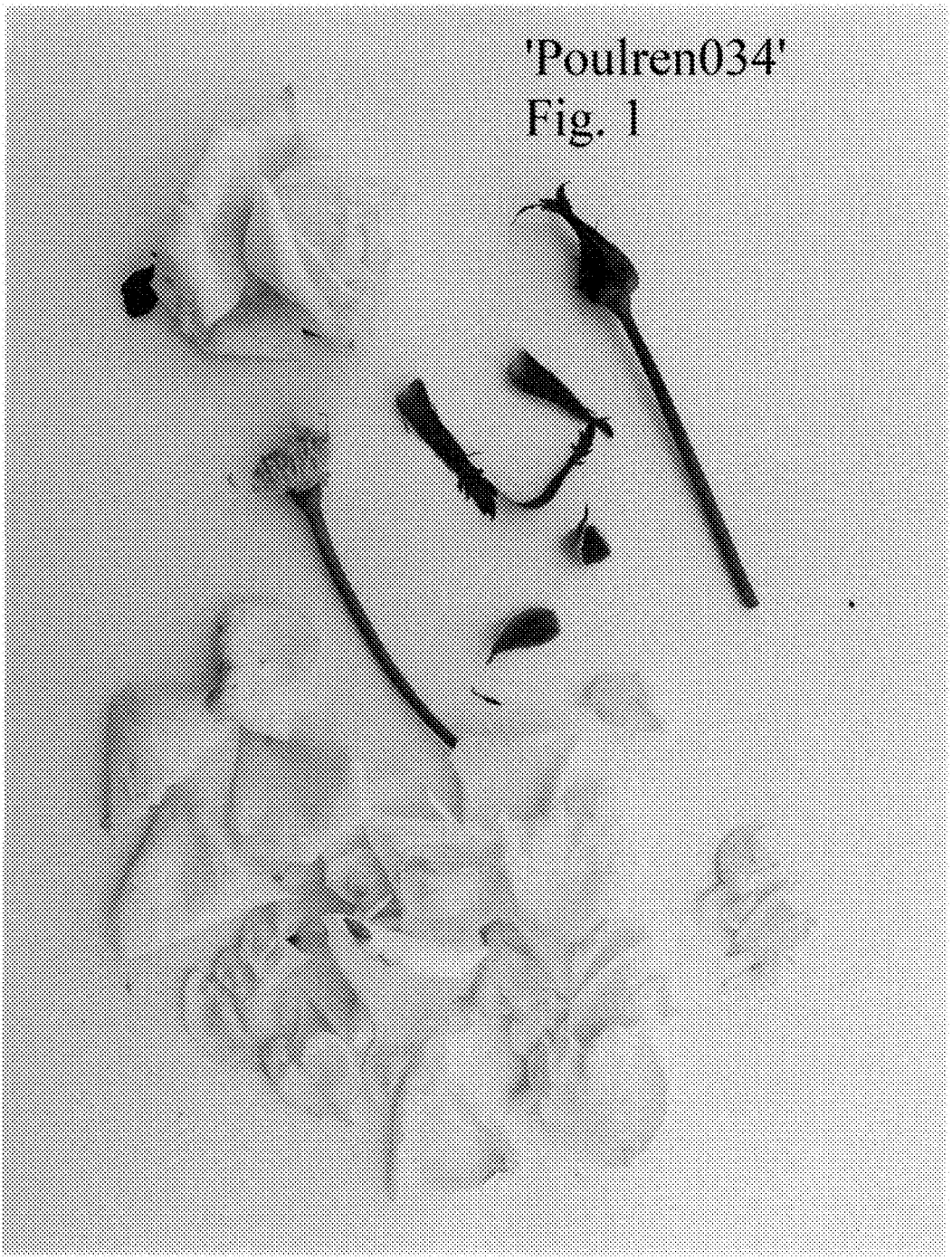
Figure 2:
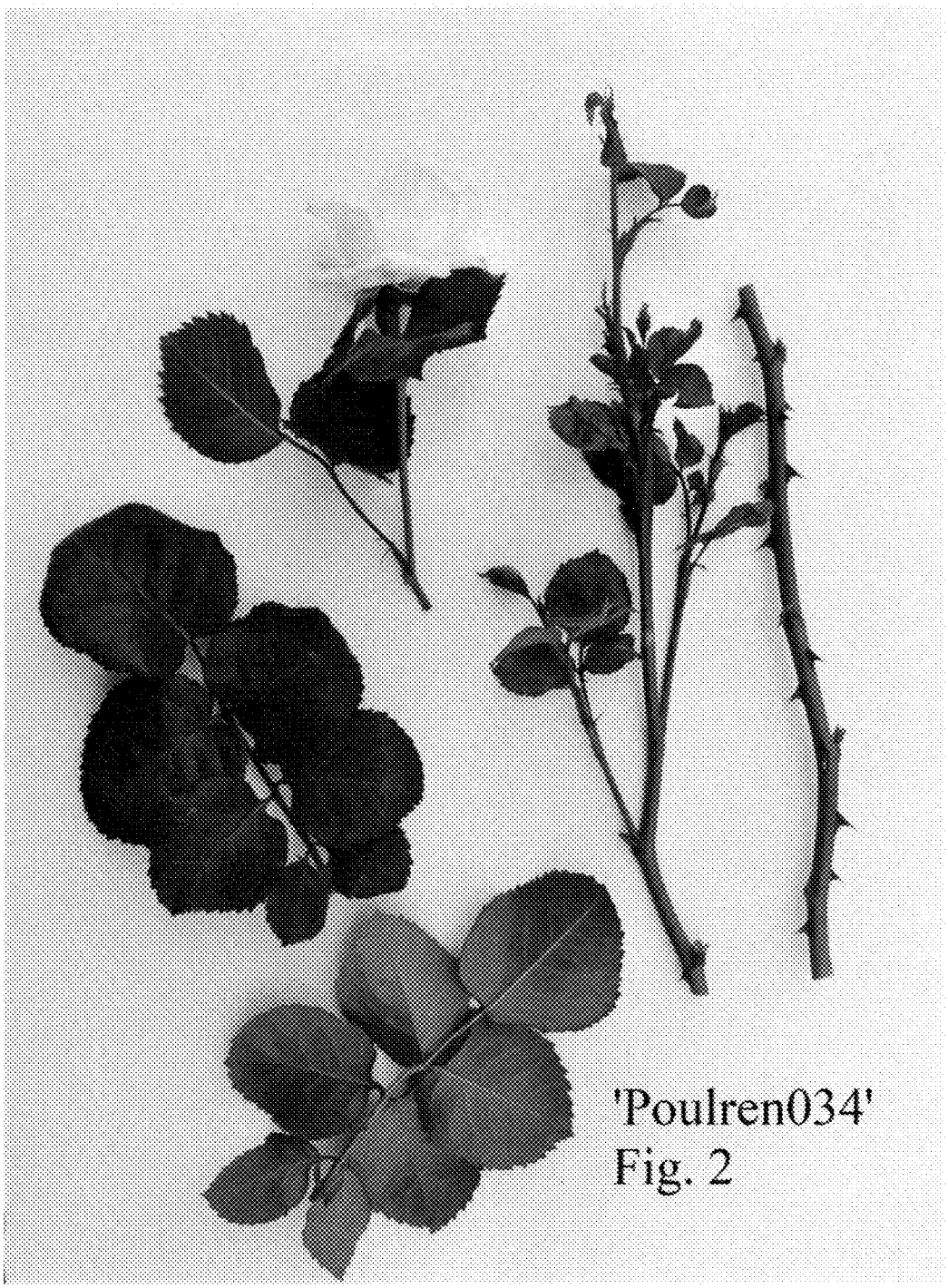
FIG. 2 illustrates mature leaves, mature stem bearing prickles, juvenile stem and leaves, and an open flower viewed from the side. Plants shown are 2 years of age.

The following is a description of 'Poulren034', as observed in its growth in an outdoor nursery in Odense Denmark. Observed plants are 18 months of age, and were grown on their own roots in 30 cm pots. Color references are made using The Royal Horticultural Society (London, England) Colour Chart, 2001, except where common terms of color are used.

For a comparison, several physical characteristics of the rose variety 'Poulht009', U.S. Plant Pat. No. 27,247 are compared to 'Poulren034'. While the claimed plant has 35 flower petals, the comparison variety has 75 petals. The claimed plant has a flower general tonality of White Group 155A and Yellow 8C. The comparison variety has a flower general tonality of White Group 155A. While the claimed plant has a flower diameter of 80 mm, the comparison variety has flowers which are 90 mm in diameter.

FLOWER AND FLOWER BUD

Blooming habit: Continuous.

Flower bud:

- *Size.*—Upon opening, 25 mm in length from base of receptacle to end of bud. Bud diameter is 14 mm.
- *Bud form.*—Urceolate, globular.
- *Sepal inner surface.*—Color: Yellow-Green Group 146D. Surface: Lightly pubescent.
- *Sepal outer surface.*—Color: Yellow-Green Group 144A and Yellow-Green Group 147A. Texture: Rough with stipitate glands.
- *Sepal shape.*—Apex: Cirrhose. Base: Flat at union with receptacle.
- *Sepal margin.*—Margins have strong foliaceous appendages on three of the five sepals.
- *Sepal size.*—42 mm long, 7 mm wide.
- *Receptacle.*—Texture: Smooth. Size: 4 mm in height, 6 mm wide. Color: Yellow-Green Group 144A. Shape: Campanulate.
- *Pedicel.*—Surface: Smooth. Length: About 80 mm. Diameter: 4 mm on average. Color: Yellow-Green Group 144A with intonations of Greyed-Orange Group 166B. Strength: Strong.

Flower bud development: Flower buds are borne single.

Flower bloom:

- *Fragrance.*—Strong perfume.
- *Duration.*—The blooms have a duration on the plant of approximately 14 days. Petals fall cleanly away from plant after flowers have fully matured.
- *Size.*—Flower diameter is 80 mm when open. Flower depth is 35 mm.
- *Flower shape.*—High centered, double, with a high pointed center which is tightly closed. Somewhat globular.
- *Shape of flower, side view.*—The upper portion is convex. The lower portion is flat concave.

Petalage: Under normal conditions, flowers have about 35 petals.

General tonality of flower: Open flowers are White Group 155A with intonations of Yellow Group 8C.

Petal color:

- *Upon opening.*—The outer and inner petals are White Group 155A on the upper surface. The lower surface is White Group 155B. At the basal zone on both sides, intonations of Yellow Group 4A.
- *After opening.*—The upper surface is Yellow Group 6D. The lower surface is White Group 155A with shades of Yellow Group 6B at the basal zone.

Petals:

- *Petal reflex.*—Strong.
- *Margin.*—Margins have small clefts, and moderate undulations.
- *Shape.*—Broad and elliptic. Apex shape: Rounded. Base shape: Acute.
- *Size.*—45 mm (l)×50 mm (w).
- *Texture.*—Smooth.
- *Thickness.*—Average.

Petaloids:

- *Size.*—30 mm (l) by 25 mm (w).
- *Quantity.*—About 6.
- *Shape.*—Elliptical and irregular. The base is acute and the apex is rounded with a cleft in the margin.
- *Color.*—Yellow Group 4D on the upper and lower surface. At the basal point of attachment Yellow Group 6B.

Reproductive flower parts:

- *Pollen.*—None observed.
- *Anthers.*—Size: 2 mm in length. Color: Yellow Orange Group 14B. Quantity: 34 on average.
- *Filaments.*—Color: Yellow Group 9A. Length: 7 mm.
- *Pistils.*—Length: 10 mm. Quantity: 27 on average.
- *Stigmas.*—Color: Yellow-White Group 158C.
- *Styles.*—Color: Yellow-White Group 158C with intonations of Red Group 47C.
- *Location of stigmas.*—Level in location relative to the length of the filaments and the height of the anthers.
- *Hips.*—None Observed.

PLANT

Plant growth: Upright. Plants are about 55 to 80 cm in height, and 42 cm wide.

Stems:

- *Color of juvenile growth.*—Yellow-Green Group 146B with intonations of Greyed-Red Group 178A.
- *Color of mature growth.*—Yellow-Green Group 146A with intonations of Greyed-Orange Group 176A.
- *Length.*—Canes are about 35 to 45 cm from the base of the plant to the flowering portion.
- *Diameter.*—About 6 mm.
- *Internodes.*—On mature canes about 40 to 45 mm between nodes.
- *Surface texture.*—Young wood: Smooth. Older wood: Smooth.

Long prickles:

- *Incidence.*—10 prickles per 10 cm of stem.
- *Size.*—Average length of prickles on mature stems is 8 mm.
- *Shape.*—Upper portion is linear. Lower portion is concave.
- *Color.*—Juvenile prickles: Greyed-Purple Group 183A. Mature prickles: Greyed-Purple Group 183A.

Plant foliage:

- *Compound leaf.*—165 mm (l)×120 (w).
- *Quantity.*—2 leaves per 10 cm of stem on average.
- *Leaf bearing angle to the stem.*—45 degrees.
- *Color of juvenile foliage.*—Upper side: Yellow-Green Group 146B with shades of Greyed-Purple Group 183A. Lower side: Yellow-Green Group 146B with shades of Greyed-Purple Group 183A.
- *Color of mature foliage.*—Upper side: Yellow-Green Group 147A. Lower side: Yellow-Green Group 146B.

Plant leaves and leaflets:

*Stipules*.—Size: 21 mm long, 3 mm wide. Quantity: 2 per compound leaf. Shape: Linear, slightly broad based with outward extending apices. Margins; Finely serrated. Color: Yellow-Green Group 144A.

*Petiole*.—Length: 20 mm. Diameter: 2 mm. Upper surface color: Yellow-Green Group 144A. Lower surface color: Yellow-Green Group 144A.

*Rachis*.—Length: About 76 mm. Upper surface color: Yellow-Green Group 144A. Lower surface color: Yellow-Green Group 144A.

*Leaflet*.—Quantity: Normally 7 leaflets. Margins: Serrated. Size: Terminal leaflets are about 70 mm long, 61 mm wide. Shape: Generally rounded. Base: Cordate. Apex: Mucronate Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulren034' substantially as described and illustrated herein.

* * * * *

'Poulren034'

'Poulren034'